United States Patent [19]

Hopka

[11] Patent Number: Plant 6,201

[45] Date of Patent: Jun. 14, 1988

[54] DISTINCT VARIETY OF STREPTOCARPUS NAMED ROSY-FINCH

[76] Inventor: Christian Hopka, 4408 Smith Dr., Deerfield, Wis. 53531

[21] Appl. No.: 858,431

[22] Filed: May 1, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Barry U. Buchbinder

[57] ABSTRACT

A new cultivar of *Streptocarpus*×*hybridus* plant is characterized by abundant production of unique rhodamine purple flowers on vigorous plants.

1 Drawing Sheet

BACKGROUND OF THE NEW PLANT

The present invention comprises a new and distinct cultivar of Cape Primrose (*Streptocarpus*×*hybridus* Voss.) known by the name of Rosy-Finch. This selection was developed for the commercial greenhouse industry as a flowering potted plant. Rosy-Finch exhibits compact, vigorous growth, improved heat tolerance, and abundant flower production under progressive commercial practices. The flower color, shape and pattern offers a novel combination not previously available.

In 1978 an ideotype breeding program was initiated to improve the characteristics of Cape Primroses for commercial production. Weismoor Hybrids, J. Innes Hybrids, "Constant Nymph" Series, Oglevees Bavarian Bells, and cultivars of unknown origin were intermated using conventional breeding procedures. $F_1$ selections were selfed and the best progenies used as background parents for the ideotype. Breeding lines were established in each of the major color classes in the $F_3$ generation. Selection criteria included floriferousness, good foliage quality and symmetrical compact habit. The pedigree of Rosy-Finch is as follows:

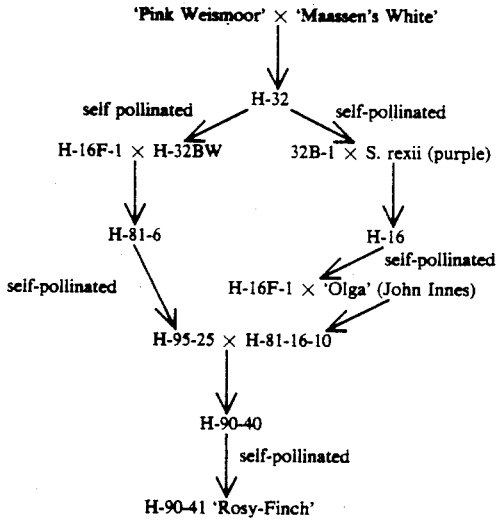

The new cultivar was first asexually reproduced by leaf cuttings in the University of Wisconsin Department of Horticulture greenhouses in Madison, Wis., in 1982.

It has been found to retain its distinctive characteristics through successive propagations.

This new cultivar was evaluated by a jury of industry specialists and professional plant breeders for aesthetic qualities, and screened though production trials for desireable propagation, production and flowering characteristics.

The new cultivar, when grown in a greenhouse in Madison, Wis. has a response time of about 11 weeks. This response time is measured from the potting of plantlets in a five inch pot to the time when the plant has six flowers. Anthesis was about 9½ weeks after potting.

A nonenabling printed publication describes Rosy-Finch (Hopka C and Beck GE (1984) Hortsci. 19:314–316).

DESCRIPTION OF THE DRAWING

The accompanying photograph illustrates the new cultivar, the colors being as nearly true as possible with color illustrations of this type. However, the most accurate representation of the colors is the description (below) referenced to The Royal Horticultural Society Colour Chart.

DESCRIPTION OF THE NEW PLANT

The botanical description of the new cultivar follows. The data was collected from asexually propagated plants produced at the University of Wisconsin-Madison, Department of Horticulture. The plant histories were taken on 14-week old plants produced in a double-layered polyethylene greenhouse under natural light. Color readings were taken indoors under cool-white fluorescent light. Color references are those displayed in The Royal Horticultural Society Colour Chart.

Botanical classification: Gesneriaceae (Family); *Streptocarpus*×*hybridus* (Genus×species).

Flower:

*Size and shape.*—Fully expanded 71 mm, Corolla gamapetalous, 5-lobed, and distinctly bilabiate.

*Borne.*—Flowers are borne in a branched cymose dichasium in clusters of one to eleven flowers.

*Color.*—Front of petals #29 Rhodamine Purple with a darker richer color in the throat and fading towards the petals periphery. Throat — (⅓) Sulphur Yellow throat lines with a White throat. Reverse of Petals — (29/2).

*Reproductive structures.*—Ovaries — length 30–33 mm and 1½ mm in diameter. Stamens — arising at base of petals and adnate for approx. 7 mm. The anterior 2 fertile, 2 lateral staminodes present. Stems — Branched, 16–18 cm long, and pubescent.

Foliage:

*Size and shape.*—Leaves oblanceolate to obovate with ruffled margins anad crenate serrations. Approx. 9.5–12.5 cm wide at the broadest point, and 23–27 cm long.

*Color.*—Top side of leaves — 0960 Spinach Green and underside color 0960/3.

Plant:

*Habit.*—Whole mature plants (8 months old) — 57 cm spread and 21 cm high.

I claim:

1. A new and distinct variety of Streptocarpus substantially as herein shown and described.

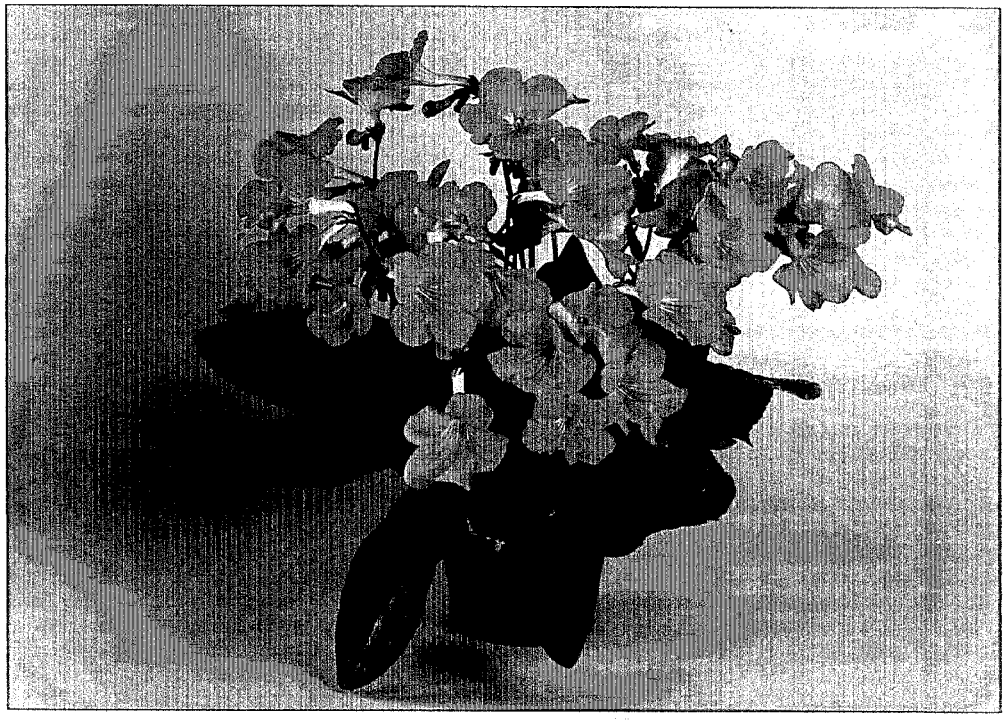

* * * * *